US006210382B1

(12) United States Patent
Hogg

(10) Patent No.: US 6,210,382 B1
(45) Date of Patent: Apr. 3, 2001

(54) EMESIS DEVICE

(76) Inventor: Chadwick B. Hogg, 23 S. Sussex Dr., Smithfield, NC (US) 27577

(*) Notice: Subject to any disclaimer, the term of this patent is extended or adjusted under 35 U.S.C. 154(b) by 0 days.

(21) Appl. No.: 09/304,652

(22) Filed: May 4, 1999

(51) Int. Cl.[7] .................... A61M 1/00
(52) U.S. Cl. .................... 604/317; 600/573
(58) Field of Search .................... 604/317, 327, 604/349, 356; 600/573; 4/258, 274, 283

(56) References Cited

U.S. PATENT DOCUMENTS 3,575,225 * 4/1971 Muheim .
3,629,873 * 12/1971 Long .
4,771,486 9/1988 Gutierrez et al. .
4,858,250 8/1989 Lee .
5,246,149 * 9/1993 Broitzman .
5,599,332 * 2/1997 Cashel .................... 604/317

* cited by examiner

*Primary Examiner*—Anhtuan T. Nguyen
*Assistant Examiner*—Michael M Thompson
(74) *Attorney, Agent, or Firm*—Lynn E. Barber

(57) ABSTRACT

An emesis device including a container having an upward opening with a front surrounding edge and front wall having a shape that accommodates placement of a human face in the opening. The device also has a handle on the back for carrying the container, indentations on the front and back for gripping the container; and a splash guard along the back edge.

12 Claims, 4 Drawing Sheets

EMESIS DEVICE

BACKGROUND OF THE INVENTION

1. Field of the Invention

This invention relates to devices for collecting and containing vomit when persons have discharged the contents of their stomach through their mouths.

2. Description of the Related Art

When people are ill with intestinal problems, have ingested substances to which they are allergic or which are harmful, have consumed excessive quantities of alcoholic beverages, or have motion sickness, they often have an uncontrollable, often violent, vomiting reaction. Such symptoms call for the use of some type of container to hold the vomited material. Even with many types of containers normally used for this purpose, the result is still often soiled clothing and surroundings. Caretakers or companions of the affected persons are themselves often soiled, especially as they attempt to clean up and provide assistance, thus resulting in additional labor for caretakers and increased costs for labor and cleaning services.

Although many types of devices have been used for this purpose, there are some containers particularly designed for this purpose. The two most common are the standard, air-sickness backs carried by most airlines and the emesis basin. The airsickness bag, while serving the basic purpose is not really sturdy enough for prolonged or repeated use, and is often difficult to hold and use so that there is no spillage due to its shape and flexibility.

A standard emesis basin is shown in FIG. 1. Generally, it is made of plastic and comprises a shallow elongated bowl originally designed to hold sputum or phlegm and not for large quantities of material. For people who have consumed much food or beverage and are very sick, the prior basin does not provide sufficient capacity, does not provide a means to keep the vomit from splashing out of the container, and is difficult to hold for an extended period. Further, although the front of the basin is gently indented to conform roughly to a person's lower face, the shape of the opening is narrow, and it is difficult to aim to emitted material so that it does not miss the container, at least in part. Th emesis basin is also relatively narrow bottomed, increasing the likelihood of inadvertent spillage of the contents.

It is therefore an object of the invention to provide an emesis device which is sufficiently large for the intended purpose, is shaped to reduce splashing, missing of the opening and spillage, and has means of assisting in gripping of the device.

Other objects and advantages will be more fully apparent from the following disclosure and appended claims.

SUMMARY OF THE INVENTION

The invention herein is an emesis device. The device comprises a container which has an upward opening having a front surrounding edge and front wall having a shape that accommodates placement of a human face in the opening, a handle on the back for carrying the container, indentations on the front and back for gripping the container; and a splash guard along the back edge. The container is of a size and shape to reduce splashing and reduce the likelihood of missing of the opening and of spillage. The container has means of assisting in holding of the device, preferably including a handle and indentations on the container.

Other objects and features of the inventions will be more fully apparent from the following disclosure and appended claims.

DETAILED DESCRIPTION OF THE INVENTION AND PREFERRED EMBODIMENTS THEREOF

The present invention is an emesis device. Generally, the container portion of the device has an upward opening having a surrounding edge with a shape that accommodates placement of a human face in the opening, a handle on the back for carrying the container, indentations on the front and back for gripping the container; and a splash guard along the back edge. The device is of a size and shape to reduce splashing and reduce the likelihood of missing of the opening and of spillage. The device has means of assisting in gripping of the device, preferably including a handle and indentations on the container.

Figure 1:
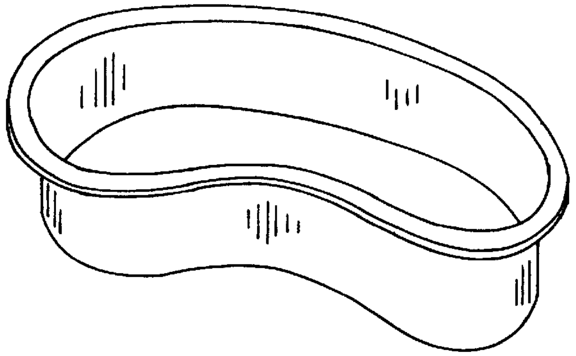
PRIOR ART FIG. 1
FIG. 1 is a perspective view of a prior art emesis basin.
Figure 2:
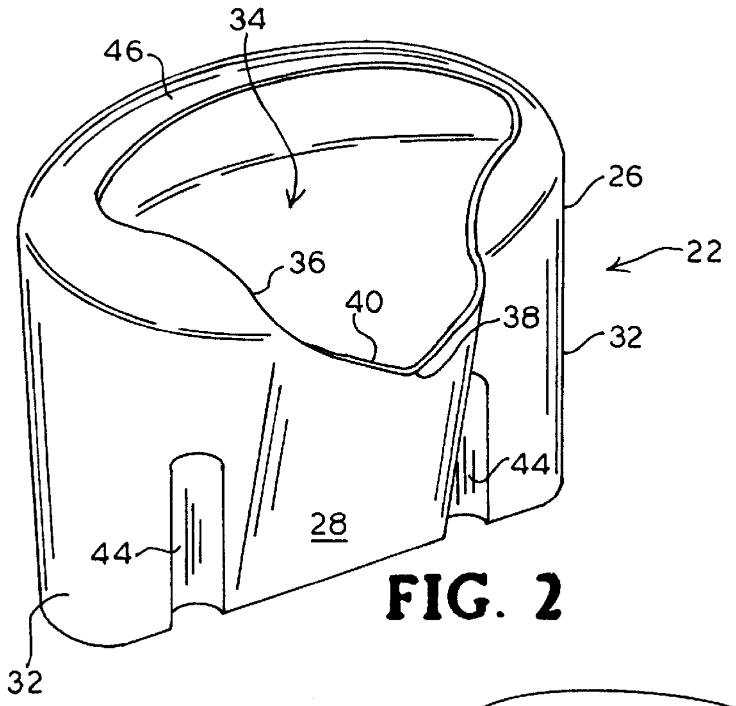
FIG. 2 is a perspective front view of a device of the invention.
Figure 3:
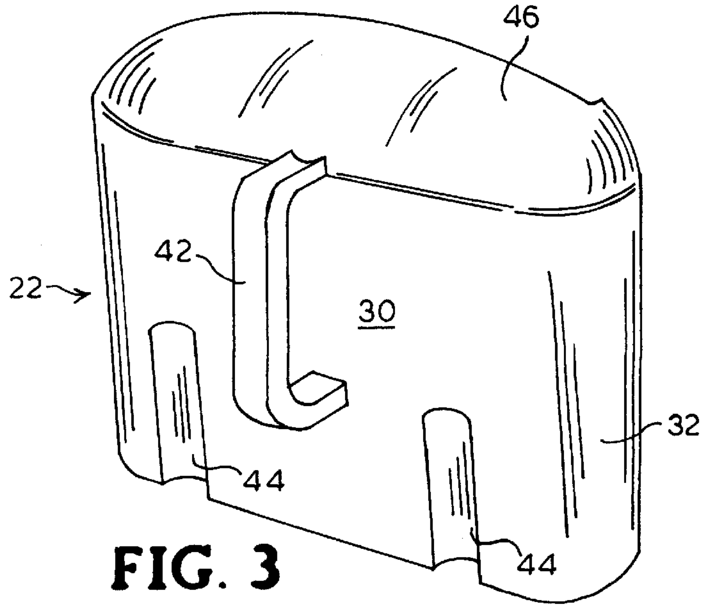
FIG. 3 is a perspective back view of a preferred embodiment of the device of the invention.

Referring in greater detail to the Figures, perspective views of the preferred embodiment are shown in FIGS. 2–3 and additional views are shown in FIGS. 4–8. The device of the invention comprises a container 22 having a base 24 and an upwardly extending wall 26 comprising a front 28, a back 30, and two ends 32. The wall has an upward opening 34 with an edge 36, comprising a back edge, surrounding the opening.

Figure 4:
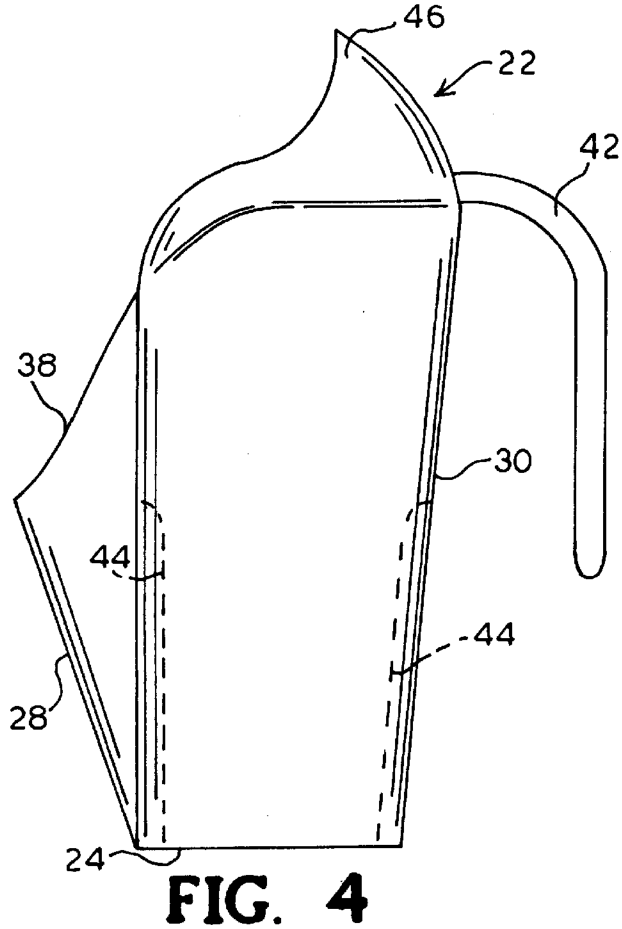
FIG. 4 is a side elevational view of the device of the invention.
Figure 5:
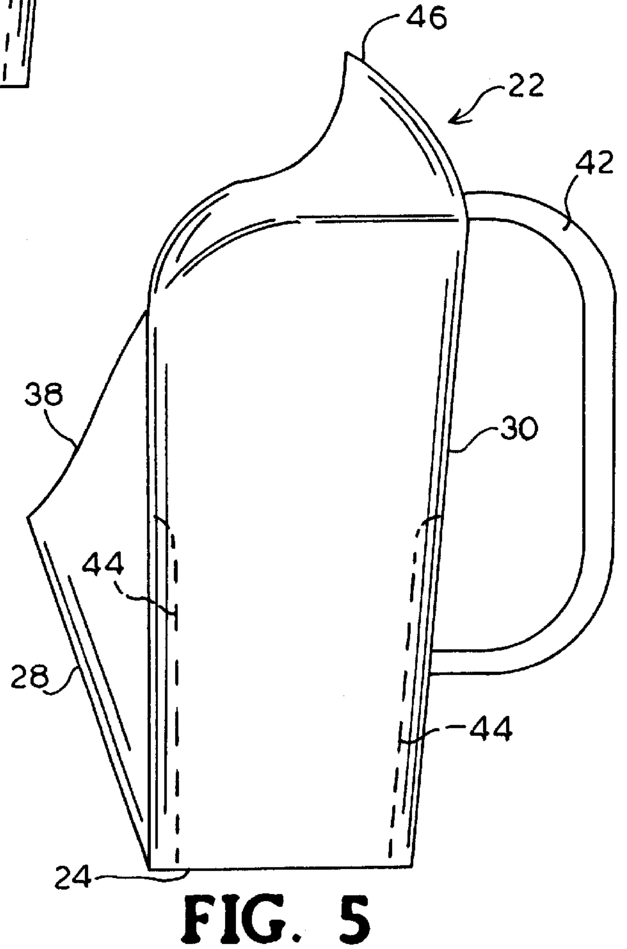
FIG. 5 is a side elevational view showing an alternative embodiment of the device of the invention.
Figure 8:
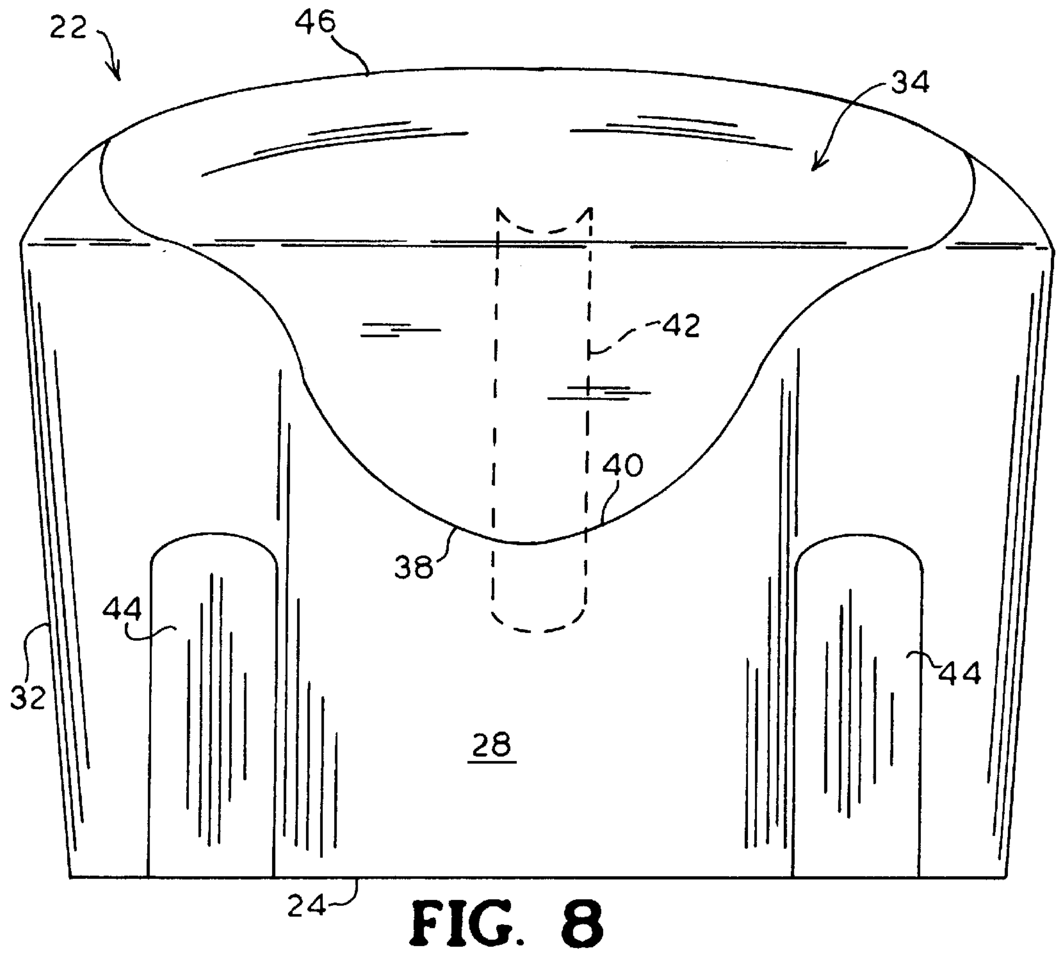
FIG. 8 is a front elevational view of the device.

Preferably the wall 26 has a shape that accommodates placement of a human face in the opening. Thus, in the preferred embodiment of the invention as shown in FIG. 2 and FIGS. 4–5, the front and the front surrounding edge have an outward contour 38 for placement of a lower face of a person. The central portion of the front wall preferably slopes away from the back wall so that the front of the opening is in a rounded "V"-shape 40 as shown in FIG. 2 and FIG. 8, where a person's jaw may be placed.

The container 22 has a handle 42, preferably on the back 30, so that the container may be easily carried. The handle 42 may be any shape, size and design. The primary types of handle that is preferred is either a handle which handle extends downward from near the back edge as shown in FIG. 4 with an unattached lower end or a handle as shown in FIG. 5 which forms a closed loop on the back of the container.

Preferably, although not required, on both the front and back of the container are means for gripping the container. These are most preferably elongated vertical indentations 44 on the front and on the back near each end of the container, but may have any other shape for gripping as would be clear to one in the art. Alternatively, there may be other types of indentation or other surface feature that assists in gripping, for example, a bumpy or textured surface that makes it easier to hold on to the container.

Figure 6:
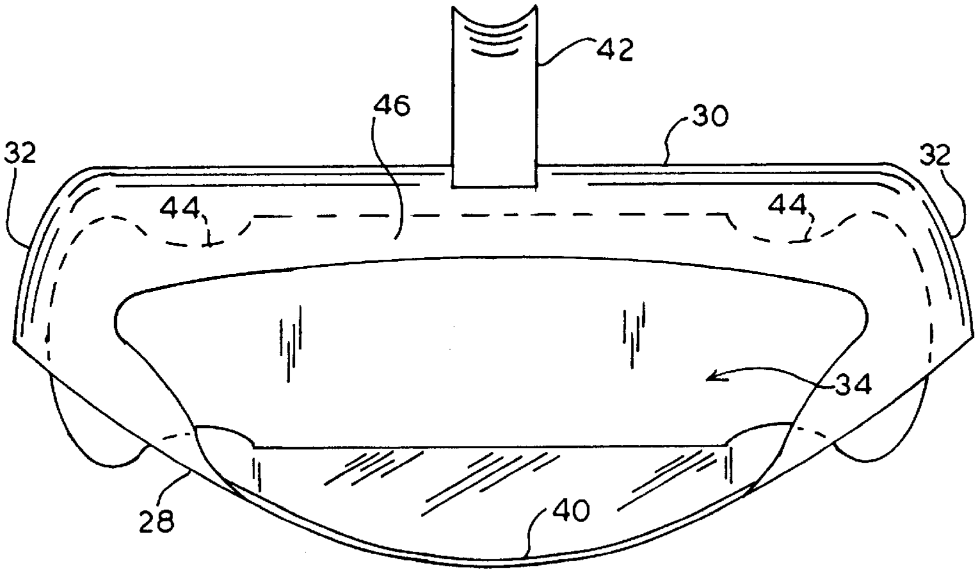
FIG. 6 is a top planar view of the device of the invention.
Figure 7:
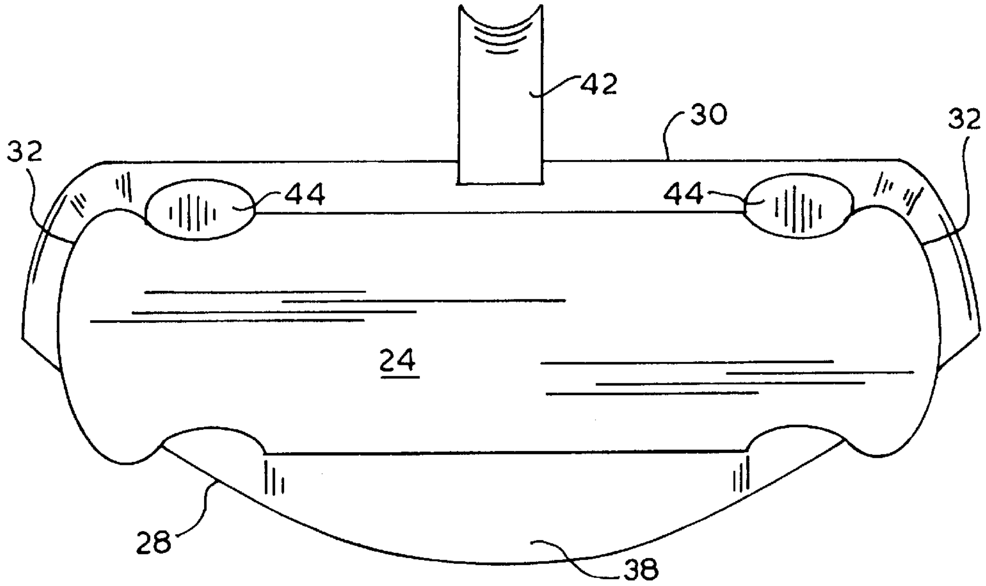
FIG. 7 is a bottom planar view of the device of the invention.

A very important feature of the device of the invention is a splash guard 46. This guard 46 preferably extends along the back edge, and most preferably extends around the edge from the outward contour near one end, around the back edge and to the outward contour on the other end as shown in FIG. 2 and FIG. 6. The splash guard 46 preferably extends at least slightly over the opening 34. For example, the portion of the splash guard along the back edge curves forward and extends partially over the opening from the back edge toward the front. Similarly, when the splash guard 46 extends around the ends these portions of the splash guard also preferably are angled inward over the opening. In a preferred embodiment, the splash guard 46 extends forward at an angle of about 125 degrees from the rear wall and at about an angle of 55 degrees from horizontal. The length of the preferred splash guard is preferably less than about 10–12 cm, and is most preferably approximately the same as the width of the basin at its widest point, for example, about 6–8 cm.

The device may be shaped so that it is stackable with other identical emesis devices, for example, by having a handle that is removable and designing the shape and taper of the sides for this purpose.

The device may be made of any material suitable for forming containers for holding liquids, such as sturdy plastics, metal and the like, and most preferably is made of a disposable substance.

While the invention has been described with reference to specific embodiments, it will be appreciated that numerous variations, modifications, and embodiments are possible, and accordingly , all such variations, modifications, and embodiments are to be regarded as being within the spirit and scope of the invention.

What is claimed is:

1. An emesis device, comprising:

(a) a container having a base, and a container wall extending upward from the base, said container wall comprising a front, a back, and two ends, said container wall having an upward opening with an edge surrounding the opening, said edge further comprising a front surrounding edge along the front angled to fit a person's jaw, and a back edge along the back, said wall having a shape that accommodates placement of a human face in the opening with the front sloping away from the back so that when a person's face is placed over the upward opening, the person's jaw fits in the angled front surrounding edge with the person's face over the upward opening;

(b) a handle on the wall for carrying the container;

(c) means on the front and back for gripping the container; and (d) a splash guard along the back edge, said splash guard angled inward over the upward opening and extending partially over the upward opening from the back toward the front surrounding edge to reduce splashing out of the container when the person vomits through the opening.

2. The device of claim 1, wherein the means for gripping the container comprises indentations on the front and back.

3. The device of claim 2, wherein there are elongated vertical indentations on the front and on the back near each end of the container.

4. The device of claim 1, wherein the front and the front surrounding edge have an outward contour for placement of a lower face of a person.

5. The device of claim 1, wherein the splash guard curves forward and extends partially over the opening from the back edge toward the front.

6. The device of claim 4, wherein the splash guard further extends around the edge from the outward contour near one end, around the back and to the outward contour on the other end.

7. The device of claim 6, wherein the splash guard along the back edge curves forward and extends partially over the upward opening from the back toward the front.

8. The device of claim 1, wherein the handle is on the back.

9. The device of claim 1, wherein the handle extends downward from near the back edge and has an unattached lower end.

10. The device of claim 1, wherein the handle forms a closed loop on the back of the container.

11. The device of claim 1, wherein the device is shaped so that it is stackable with other identical emesis devices.

12. The device of claim 1, wherein the device is disposable.

* * * * *